United States Patent [19]

Matthews et al.

[11] Patent Number: 5,057,613
[45] Date of Patent: Oct. 15, 1991

[54] NOVEL THIONE DOPAMINE BETA HYDROXYLASE INHIBITORS

[75] Inventors: Donald P. Matthews; James R. McCarthy, both of West Chester, Ohio; Jeffrey P. Whitten, Zionsville; Robert J. Broersma, Jr., Noblesville, both of Ind.

[73] Assignee: Merrell Dow Pharmaceuticals, Cincinnati, Ohio

[21] Appl. No.: 114,168

[22] Filed: Oct. 27, 1987

Related U.S. Application Data

[63] Continuation-in-part of Ser. No. 860,263, May 6, 1986, abandoned.

[51] Int. Cl.$^5$ ........................................... C07D 409/06
[52] U.S. Cl. ...................................................... 548/318
[58] Field of Search .......................................... 548/318

[56] References Cited

U.S. PATENT DOCUMENTS 3,915,980 10/1975 Gebert et al. ..................... 260/309
4,634,711 1/1987 Kaiser et al. ...................... 514/341
4,749,717 5/1988 Kouse ................................ 514/392

FOREIGN PATENT DOCUMENTS 0688585 4/1967 Belgium .
0125033 11/1984 European Pat. Off. .............. 233/84
0221778 5/1987 European Pat. Off. .............. 233/84
2304508 8/1973 Fed. Rep. of Germany ...... 548/318
1155580 6/1969 United Kingdom .

OTHER PUBLICATIONS

Lawrence I. Kruse, et al., *J. Med. Chem.*, 29,887–889 (1986).
Belgodere, Heterocycles, 20, 2019 (1983).
Stephen T. Ross, et al., *J. Med. Chem.*, 30, 1309–1313 (1987).

*Primary Examiner*—Robert Gerstl
*Attorney, Agent, or Firm*—John J. Kolano

[57] ABSTRACT

Imidazole-2-thione derivatives useful as antihypertensive agents are described herein. The compounds are obtained by cyclization of an appropriate open-chain compound such as an appropriately substituted thiourea.

3 Claims, No Drawings

NOVEL THIONE DOPAMINE BETA HYDROXYLASE INHIBITORS

The present application is a continuation-in-part of application Ser. No. 860,263, filed May 6, 1986 and now abandoned.

This invention relates to novel derivatives of 1-substituted imidazoles, to the processes and intermediates useful for their preparation, to the pharmaceutical compositions containing said imidazoles, to their dopamine beta-hydroxylase inhibiting pharmacological activity and to their applied use in the treatment of hypertension.

More specifically, this invention relates to novel 1-imidazole derivatives of the formula

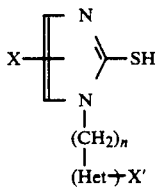

I including the 2-thione tautomers thereof, wherein n is 2, or 4; X is hydrogen, $C_{1-6}$ lower alkyl, chloro, bromo, phenyl, benzyl, or Z-substituted phenyl or benzyl with Z being $C_{1-6}$ lower alkyl or halogeno; (Het) is a heterocycle of the group consisting of thienyl, furyl, pyridinyl, pyrazolyl, pyrimidinyl, pyrrolyl, thiazolyl and imidazol-2-yl; and X' is hydrogen, halogen or $C_{1-6}$ lower alkyl. The compounds show a dopamine beta-hydroxylase inhibiting activity and are useful in the treatment of hypertension.

Formula I above shows the compounds of the present invention as thiols but the compounds tautomerize readily to the corresponding 2-thiones and the two forms are considered as equivalent. Thus any description or reference to a 1,3-dihydro-2H-imidazole-2-thione should be considered as a description or reference to the corresponding 1H-imidazole-2-thiol or vice versa.

The "lower alkyl" groups referred to above are straight or branched-chain hydrocarbyl radicals having up to six carbon atoms, preferably methyl, ethyl and propyl; the halogen groups referred to above are illustrated by chloro, fluoro or bromo; in the Z substituted phenyl or benzyl referred to above, those substituents can be at the ortho or meta positions, but preferably they are located at the para- position. The heterocycle terms represented by "Het" in formula I can be exemplified by 2- and 3-thienyl; 2- and 3-furyl; 2-, 3- and 4-pyridinyl; 2-, 4- and 5-pyrimidinyl; 2- and 3-pyrrolyl and their 2,5-dihydro 1H-pyrrolyl analogs; and 3-, 4- and 5-pyrazolyl and its 4,5-dihydro analogs. These heterocyclic moieties may be unsubstituted or they may also contain halogeno or lower alkyl substituents at any of their open positions, i.e., X' is hydrogen, halogeno or $C_{1-6}$ lower alkyl. Those compounds in which Het is thienyl are preferred. The heterocyclic moiety (i.e., Het) is attached to the nitrogen atom of the imidazole moiety through an alkylene bridging moiety having two to four carbon atoms and such alkylene groups are illustrated by ethylene, trimethylene and tetramethylene. Those compounds in which n is 2 (i.e., the bridging group is ethylene) are preferred.

In the preparation of the compounds of this invention it is quite obvious that the specific compound sought to be prepared will have a bearing on the particular process path to be utilized. Such factors as the specific X, X' and/or Z substituents, the particular alkylene bridge present between the imidazolyl moiety and its attached heterocycle, and ready availability of the starting materials all play a role in choosing the specific path to be followed in the preparation of the compounds of this invention. Those factors are readily appreciated by one of ordinary skill in the art. However, in general, the compounds of this invention may be prepared by standard techniques and processes analogously known in the art.

In those instances wherein the compounds sought to be prepared contain a sulfhydryl substituent on the imidazole ring moiety, it is convenient to react an isothiocyanate derivative (II) with an appropriate amino acetal (III) to form a thiourea reaction product (IV), which is treated with acid to hydrolyze the acetal whereupon a cyclization reaction takes place to form the imidazole ring bearing the sulfhydryl substituent (Ia). These reactions are depicted in Reaction Scheme A in which (III) is shown as the methyl acetal although, obviously, the ethyl acetal could also be used.

REACTION SCHEME A

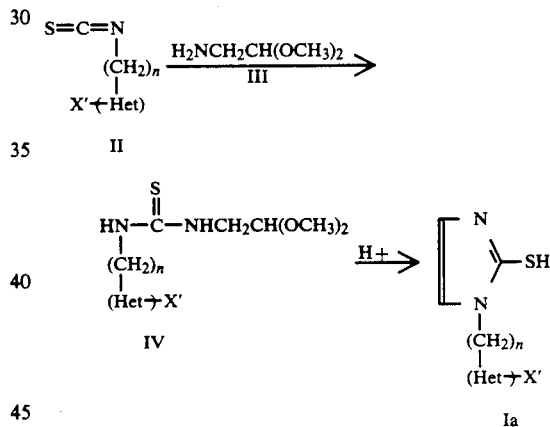

wherein Het, n, X, X', $R_1$ and $R_2$ are as defined in formula I.

Although it is not specifically shown in the Reaction Scheme above, the acetal (III) can be substituted at either position on the two-carbon chain by a group X wherein X is alkyl, phenyl, benzyl or substituted phenyl or benzyl and this would give the correspondingly substituted imidazole on cyclization of the thiourea obtained first. In those instances wherein it is desired to prepare a halogenated derivative, i.e., X in formula I is chloro or bromo, then the thione (Ia) is appropriately protected and the protected compound is halogenated according to procedures well known in the art.

The reaction of the isothiocyanate derivatives (II) with the acetal (III) is a simple condensation reaction, preferably effected by heating the reactants under reflux conditions using inert solvents, e.g., toluene or DMF at 80° C., to form the thiourea (IV) intermediates. These intermediates are subjected to cyclization by treatment with acid, preferably by refluxing the intermediates with aqueous hydrochloric acid in ethanol to produce the desired 1-substituted-2-imidazole bearing a sulfhydryl substituent (Ia).

The present 1-hetero-2-imidazoles (Ic) may also by prepared by treating a heteroaldehyde derivative (V) with the aforementioned acetals (III) to form a Schiff base which is reduced to form an intermediate (VI) which is subjected to a cyclization reaction by treatment with aqueous HCl in ethanol in the presence of an alkali metal isothiocyanate, preferably KSCN. These reactions may be depicted by the following reaction scheme.

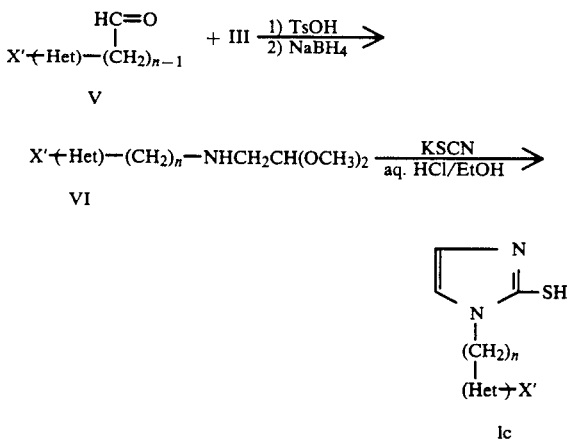

wherein (Het), X' and n are defined as above.

The isothiocyanates used as the starting materials in Reaction Scheme A are prepared, by the reaction of the appropriate amine with 1'-thiocarbonyldiimidazole. The amine used can, in turn, be obtained by reduction of the corresponding nitrile. Diborane is a useful reagent for the reduction of such a nitrile. The nitrile itself can be obtained by the reaction of an alkali metal cyanide with a compound of the formula

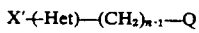

wherein Het, X' and n are defined as above and Q is a 4-toluenesulfonyloxy or a similar leaving group or a halogen such as chloro or bromo. The indicated sulfonyloxy compounds are obtained by the reaction of the appropriate alcohol and sulfonyl chloride.

The following examples merely illustrate the various techniques and procedures utilized for the preparation of the compounds of this invention; it being understood that they are not meant to limit the scope of the compounds defined by this invention.

EXAMPLE 1

1,3-Dihydro-1-(2-thienylmethyl)-2H-imidazole-2-thione

A mixture of 33.6 g (0.3 mol) thiophene-2-carboxaldehyde, 39.9 g (0.3 mol) aminoacetaldehyde diethyl acetal, 0.3 g of 4-toluenesulfonic acid (TsOH) and 200 ml ethanol is placed in a 500 ml flask and heated to reflux. After 2 hours, the reaction is concentrated and the residue dissolved in 250 ml ethanol. Solid NaBH4 (12.5 g, 0.33 mol) is added in small portions. The reaction is refluxed for 1½ hours, cooled to room temperature and poured into cold water. The product is extracted into CH2Cl2 (2×250 ml). After drying (Na2SO4) and concentration, 66.7 g crude product is obtained as a pale yellow oil. 22.9 g (0.1 mol) of the crude amine is placed in a 500 ml flask along with 11.7 g (0.12 mol) KSCN, 150 ml ethanol, 40 ml water and 15 ml concentrated hydrochloric acid. After refluxing for 5 hours, the reaction is poured onto 1 liter of ice water. The white crystals are collected and dried to give 12.0 g (61%) product, mp 128°–130° C. (EtOH).

EXAMPLE 2

1,3-Dihydro-1-(2-thienylmethyl)-2H-imidazole-2-thione

Under a blanket of nitrogen, 11.3 g (0.1 mol) 2-aminomethylthiophene is added to 19.6 g (0.11 mol) 1,1'-thiocarbonyldiimidazole in 200 ml anhydrous toluene at 0° C. the reaction is held at 0° C. for 4 hours. Then 10.5 g (0.1 mol) aminoacetaldehyde dimethyl acetal is added and the reaction is warmed at 80° C. for 2 hours. The toluene is removed and the residue dissolved in 100 ml ethanol, 15 ml water and 15 ml concentrated HCl. The mixture is refluxed 5 hours, cooled and poured into 1 L ice. After recrystallization (1/1 EtOH/H2O) the desired product is obtained as white shiny crystals, mp 128°–130° C.

EXAMPLE 3

1,3-Dihydro-1-(2-thienyl)-2H-imidazole-2-thione

A mixture of 2-isothiocyanatothiophene (16.9 g, 0.12 mol) and aminoacetaldehyde dimethyl acetal (12.6 g, 0.12 mol) in 200 ml toluene is refluxed for 2 hours. After removal of the toluene, the residue is dissolved in 200 ml ethanol and 45 ml conc. HCl added. After the reaction is refluxed for 5 hours, it is poured onto ice. The product is collected and purified by recrystallization.

In a similar manner, by following the generic teachings related to Reaction Schemes A or B and by substantially following the procedures of the foregoing examples, there may be prepared the following 1,3-dihydro-2H-imidazole-2-thiones:

5-chloro-1-(2-thienylmethyl)-1,3-dihydro-2H-imidazole-2-thione,
5-bromo-1-(2-thienylmethyl)-1,3-dihydro-2H-imidazole-2-thione,
5-methyl-1-(2-thienylmethyl)-1,3-dihydro-2H-imidazole-2-thione,
4-phenyl-1-(2-thienylmethyl)-1,3-dihydro-2H-imidazole-2-thione,
5-benzyl-1-(2-thienylmethyl)-1,3-dihydro-2H-imidazole-2-thione, The corresponding 1-[2-(2-thienyl)ethyl], 1-[3-(2-thienyl)propyl], and 1-[4-(2-thienyl)butyl] homologs are likewise obtained in a similar way.

Similarly, the corresponding analogs of the foregoing may be prepared for the corresponding 1-position pyrazolyl, furyl, pyrimidinyl, pyrrolyl and imidazolyl substituted 1,3-dihydro-2H-imidazole-2-thiones.

EXAMPLE 4

1,3-Dihydro-1-[3-(2-thienyl)propyl]-2H-imidazole-2-thione

A mixture was prepared from 20.8 g of 2-[2-(4-toluenesulfonyloxy)ethyl]thiophene, 5.4 g of sodium cyanide and 175 ml of dimethylsulfoxide and this mixture was heated to 90° C. The mixture was quenched by pouring it into saturated aqueous ammonium chloride solution and the resulting solution was extracted into ethyl acetate. The ethyl acetate solution was dried over sodium sulfate and the solvent was evaporated under reduced pressure to give crude 2-thiophenepropionitrile. This product was mixed with 175 ml of 1M diborane in tetrahydrofuran and allowed to stir at room temperature. The reaction was quenched in ethanol and methanolic hydrogen chloride was added. The white solid which formed was separated by filtration, washed with ether and dried in a vacuum oven to give 3-(2-thienyl)propylamine hydrochloride melting at about 197°-198° C.

A solution of 4.1 g of 3-(2-thienyl)propylamine (obtained from the hydrochloride by standard procedures) in about 100 ml of dimethylformamide was cooled to 0° C. and 5.7 g of solid 90% 1,1'-thiocarbonyldiimidazole was added. The mixture was allowed to warm slowly to room temperature and then stirred for 16 hours. It was then poured into water and the resulting aqueous mixture was extracted with three portions of ethyl acetate. Saturated sodium chloride solution was added to break up any emulsion. The resulting ethyl acetate solution was washed with water, dried over sodium sulfate and then concentrated. The crude product obtained was mixed with 3.0 g of aminoacetaldehyde dimethyl acetal in 80 ml of dimethylformamide and heated at 80° C. for 3 hours. The mixture was then cooled to room temperature and the solvent was removed under reduced pressure. The residue was dissolved in ethanol and 2.5N hydrochloric acid was added to hydrolyze the acetal. The mixture was heated at reflux for 2 hours and then cooled to room temperature and poured into 500 g of ice. The resulting mixture was then heated to remove any remaining ethanol but no solid formed in the residual mixture which was then extracted with three portions of ethyl acetate. The ethyl acetate extracts were combined and dried over sodium sulfate and the solvent was evaporated to give a residual tan oil. This oil crystallized on standing and was recrystallized from toluene to give 1,3-dihydro-1-[3-(2-thienyl)propyl]-2H-imidazole-2-thione melting at about 94°-96.5° C.

EXAMPLE 5

1,3-Dihydro-1-[2-(2-thienyl)ethyl]-2H-imidazole-2-thione

To 4000 ml of 1M diborane/tetrahydrofuran there was added 170 g of 2-thiopheneacetonitrile over a period of 30 minutes. The reaction temperature gradually warmed to 47° C. during the addition and the mixture was then allowed to cool to room temperature and stand and stir for 5 days. The colorless reaction was quenched by the addition of 800 ml of ethanol followed by 300 ml of saturated methanolic hydrogen chloride until the mixture became acidic. The solid which precipitated from the solution was collected by filtration, washed with ether and then dried in a vacuum oven at 50° C. to give 2-(2-thienyl)ethylamine hydrochloride melting at about 198°-200° C.

2-(2-Thienyl)ethylamine (91 g, obtained by partitioning the hydrochloride salt between ethyl acetate and ice cold 2N sodium hydroxide, washing the organic layer with brine, drying with sodium sulfate and evaporating the solvent in vacuo to a colorless oil) in 500 ml of dimethylformamide was added all at once to an ice cooled solution of 142 g of 90% 1,1'-thiocarbonyldiimidazole in dimethylformamide. The mixture was stirred for 16 hours at room temperature and then poured into 4000 ml of brine. The resulting solution was extracted with three portions of ethyl acetate and the combined organic layers were washed with water and dried over sodium sulfate and the solvent was evaporated to leave a residual oil which was the isothiocyanate corresponding to the starting amine. To a solution of 194 g of this crude isothiocyanate in 300 ml of dimethylformamide there was added 75 g of aminoacetaldehyde dimethyl acetal. The reaction warmed to 70° C. and was further heated at 80° C. for 2.5 hours. After the mixture was cooled to room temperature, the dimethylformamide was removed by Kugelrohr distillation. The residual orange oil was mixed with 500 ml of 10% aqueous hydrochloric acid and 300 ml of ethanol and heated at a gentle reflux for 2 hours. The resulting solution was cooled and poured onto 3 liters of ice with stirring. Crystallization was induced by the addition of a seed crystal and the solid which formed was separated by filtration and dried in a vacuum oven at 50° C. It was then recrystallized from toluene to give 1,3-dihydro-1-[2-(2-thienyl)ethyl]-2H-imidazole-2-thione melting at about 131°-134° C. This compound has the following structural formula:

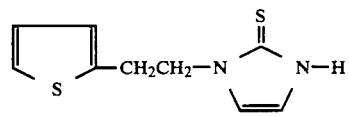

EXAMPLE 6

If the appropriate alcohol is used as the starting material and it is reacted with 4-toluenesulfonyl chloride to give the corresponding sulfonate ester which is then further reacted according to the procedure described in Example 4, or the appropriate nitrile is used as the starting material and it is further reacted according to the procedures described in Examples 4 or 5, the following compounds are obtained:

1,3-Dihydro-1-[2-(5-chloro-2-thienyl)ethyl]-2H-imidazole-2-thione.

1,3-Dihydro-1-[2-(5-bromo-2-thienyl)ethyl]-2H-imidazole-2-thione.

1,3-Dihydro-1-[2-(5-methyl-3-thienyl)ethyl]-2H-imidazole-2-thione.

1,3-Dihydro-1-[2-(2-methyl-3-thienyl)ethyl]-2H-imidazole-2-thione.

1,3-Dihydro-1-[2-(5-chloro-2-furyl)ethyl]-2H-imidazole-2-thione.

1,3-Dihydro-1-[2-(5-bromo-2-furyl)ethyl]-2H-imidazole-2-thione.

1,3-Dihydro-1-[2-(5-methyl-2-furyl)ethyl]-2H-imidazole-2-thione.

1,3-Dihydro-1-[3-(5-methyl-2-furyl)propyl]-2H-imidazole-2-thione.

1,3-Dihydro-1-[4-(5-methyl-2-thienyl)butyl]-2H-imidazole-2-thione.

1,3-Dihydro-1-[2-(5-chloro-1-methyl-1H-imidazol-2-yl)ethyl]-2H-imidazole-2-thione.

1,3-Dihydro-1-[2-(1H-pyrazol-3-yl)ethyl]-2H-imidazole-2-thione.

1,3-Dihydro-1-[2-(4-bromo-1H-pyrrol-2-yl)ethyl]-2H-imidazole-2-thione.

1,3-Dihydro-1-[2-(4-chloro-1H-pyrrol-2-yl)ethyl]-2H-imidazole-2-thione.

1,3-Dihydry-1-[2-(4-methyl-2-thiazolyl)ethyl]-2H-imidazole-2-thione.

1,3-Dihydro-1-[2-(6-chloro-2-pyridinyl)ethyl]-2H-imidazole-2-thione.

1,3-Dihydro-1-[2-(4-methyl-2-pyridinyl)ethyl]-2H-imidazole-2-thione.

1,3-Dihydro-1-[2-(5-methyl-2-pyridinyl)ethyl]-2H-imidazole-2-thione.

1,3-Dihydro-1-[2-(6-methyl-4-pyrimidinyl)ethyl]-2H-imidazole-2-thione.

The compounds of this invention exhibit valuable in vitro and in vivo pharmacological effects in that they are dopamine beta-hydroxylase (DBH) inhibitors and thus would be valuable therapeutic agents useful in the treatment of hypertension.

The DBH inhibitory compounds of this invention can readily be determined in vitro by standard and well known procedures for assaying conversion of tyramine to octopamine in the presence of dopamine beta-hydroxylase (DBH). Enzymatic oxygenation by DBH is determined in aqueous solution in the presence of molecular oxygen, an electron donor such as ascorbate, and the necessary cofactors for the enzyme at pH of 5 and a temperature of 20°-40° C., preferably 37° C. The test compound is added at the desired concentration, and the system is incubated. Activity is determined by measuring the oxygen uptake using a polarographic electrode and an oxygen monitor by the method of S. May, et al., *J. Biol. Chem.* 256, 2258 (1981). Inhibition is given in molar concentration of compound at which DBH activity was halved ($IC_{50}$) when the test compounds were tested according to the above described procedure. The $IC_{50}$ (expressed in micromolar units) data of some of the compounds of this invention are expressed in Table I.

The compounds of this invention may also be tested for their in vivo DBH inhibiting property according to the procedure of Felice, Felice and Kessinger, *J. Neurochem.*, 31, 1461-1465 (1978) wherein the effects on peripheral dopamine and norepinephrine levels are determined. In this test spontaneously hypertensive rats are dosed (i.p.) at 50 mg per kilogram of body weight and sacrificed six hours later. Average results, expressed in micrograms of dopamine (DA) per gram of heart tissue are determined with the difference between the control and the treated rats being the in vivo (DBH) inhibitory effect of the test compound. Results on some of the compounds of this invention are shown in Table I.

The ability of the compounds of this invention to lower blood pressure can be determined in vivo using spontaneously hypertensive rats (SHR's) according to standard and well known procedures. The test compound is administered intraperitoneally (ip) to rats and the blood pressure monitored continuously. Since DBH is a major enzyme in the synthetic pathway of the catecholamines, it would be expected that the presence of an inhibitor would act to decrease the amount of catecholamines produced, and thereby have an antihypertensive effect. The results of the testing for this antihypertensive effect are shown in Table I (MBP is mean blood pressure).

TABLE 1

Inhibition of DBH In Vitro and
In Vivo at 50 mg/kg, IP, 6 Hours Post Dose in SHR's*

| Compound | $IC_{50}$ ($\mu$M) | Heart DA ($\mu$g/g) | Max Change MBP(mmHg) |
|---|---|---|---|
| 1 | 0.12 | Control 0.015 ± .002 Treated 0.038 ± .003*** | −45 ± 17[a] |
| 2 | 1.86 | — | — |

*Spontaneously Hypertensive Rats.
***p < .001.
[a]Mean Difference ± Standard Deviation.
Compound 1 — 1,3-Dihydro-1-[2-(2-thienyl)ethyl]-2H-imidazole-2-thione
Compound 2 — 1,3-Dihydro-1-[3-(2-thienyl)propyl]-2H-imidazole-2-thione Based on the foregoing test results, as well as by comparison with similar test results for compounds known to be useful, the compounds of this invention exert their DBH inhibiting effects (i.e., their $IC_{50}$ effects) at from 0.1 to 100 micromolar concentrations and are expected to exhibit end-use antihypertensive activity at doses of about 1 mg to 100 mg per kilogram of body weight.

As stated above, the compounds of this invention are useful in the treatment of hypertension. In the management of hypertension, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 100 mg per kilogram of patient body weight per day, which can be administered in single or multiple doses. Naturally these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions according to standard procedures generally known in the art.

About 1 to 100 mg of a compound or mixture of compounds of Formula I is compounded with a physiologically acceptable vehicle carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

What is claimed is:

1. A compound of the formula:

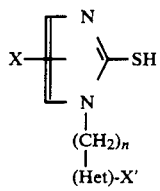

including the 2-thione tautomers thereof, wherein n is 2, 3 or 4; X is hydrogen, chloro, bromo, $C_{1-6}$ alkyl, phenyl or benzyl; Het is thienyl; and X' is hydrogen, halogen or $C_{1-6}$ alkyl.

2. A compound of the formula:

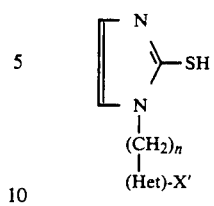

including the 2-thione tautomers thereof, wherein n is 2, 3 or 4; Het is thienyl; and X' is hydrogen, halogen or $C_{1-6}$ alkyl.

3. A compound which is 1,3-dihydro-1-[2-(2-thienyl)ethyl]-2H imidazole 2-thione.

* * * * *

UNITED STATES PATENT AND TRADEMARK OFFICE
CERTIFICATE OF CORRECTION

PATENT NO. : 5,057,613

DATED : October 15, 1991

INVENTOR(S) : Donald P. Matthews; James R. McCarthy; Jeffrey P. Whitten and Robert J. Broersma, Jr.

It is certified that error appears in the above-identified patent and that said Letters Patent is hereby corrected as shown below:

At Column 1, lines 26 and 27, the patent reads "wherein n is 2, or 4;" and should read --wherein n is 2,3 or 4;--.

At Column 3, line 34, the patent reads "with 1'-thiocarbonyldiimidazole," and should read --with 1,1'thiocarbonyldiimidazole.--.

Signed and Sealed this

Sixth Day of April, 1993

Attest:

STEPHEN G. KUNIN

*Attesting Officer*   Acting Commissioner of Patents and Trademarks